US United States Patent [19]

Matier et al.

[11] 4,321,398
[45] Mar. 23, 1982

[54] THIENYL AND BENZOTHIENYL-TERTIARY BUTYLAMINOPHENOXYPROPANOLS

[75] Inventors: William L. Matier, Libertyville, Ill.; William E. Kreighbaum, Evansville, Ind.

[73] Assignee: Mead Johnson & Company, Evansville, Ind.

[21] Appl. No.: 261,419

[22] Filed: May 7, 1981

[51] Int. Cl.³ .................. C07D 333/20; C07D 333/58
[52] U.S. Cl. ..................................... 549/58; 424/275; 549/74
[58] Field of Search ................................. 549/58, 74

[56] References Cited

U.S. PATENT DOCUMENTS 3,337,628  8/1967  Crowther et al. ............... 260/570.7
4,234,595  11/1980  Kreighbaum et al. ............. 424/274

FOREIGN PATENT DOCUMENTS 25727  3/1981  European Pat. Off. .

OTHER PUBLICATIONS

Goldberg et al., Eur. J. Med. Chem.–Chimica Therapeutica, vol. 9, No. 2 (1974) pp. 123–127.
Royer et al., Eur. J. Med. Chem.–Chimica Therapeutica, vol. 14, No. 5 (1979) pp. 467–469.
Derwent No. 90712 C/51.

Primary Examiner—Richard Raymond
Attorney, Agent, or Firm—Robert H. Uloth; Robert E. Carnahan

[57] ABSTRACT

Substituted 1-phenoxy-3-(thienyl-tert.-butylamino)-2-propanols and related 3-benzothienyl compounds are selective β-receptor blocking agents. Preferred compounds bear an ortho-substituent on the phenoxy ring.

7 Claims, No Drawings

THIENYL AND BENZOTHIENYL-TERTIARY BUTYLAMINOPHENOXYPROPANOLS

FIELD OF THE INVENTION

The present invention is concerned with heterocyclic carbon compounds of the thiophene series having an amino substituent (Class 549, Subclass 74), and with drug, bio-affecting and body-treating processes employing these compounds (Class 424/275).

BACKGROUND OF THE INVENTION

A substantial body of prior art has evolved over the last decade involving compounds of the 3-aryloxy-2-hydroxypropylamine series which have β-adrenergic properties and are useful in the treatment of cardiovascular diseases. These structures are typified by propranolol (formula 1); chemically, 1-isopropylamino-3-(1-naphthoxy)-2-propanol. Propranolol and some related naphthoxypropanolamines are the subject of U.S. Pat. No. 3,337,628 issued Aug. 22, 1967. Numerous subsequent patents have been granted covering carbocyclic ethers in which other aromatic rings or heterocyclic systems replace the naphthoxy group of propranolol.

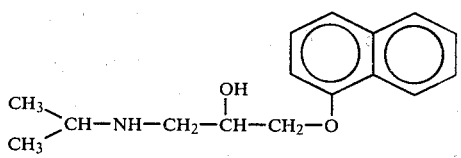

Certain benzo[b]thiophenoxy series of compounds of formula (2)

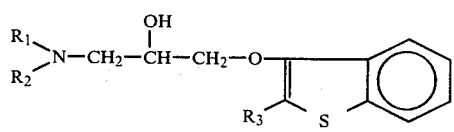

having β-adrenergic blocking properties were described in:

Goldenberg, et al., *Eur. J. Med. Chem.-Chemica Therapeutica*, 9/2, 123–127 (1974).

Royer, et al., ibid. 14/5, 467–469 (1979).

Agence Nat. Valorisation, E.P. 20-266 patented Dec. 10, 1980.

In these series, the benzothienyl system has been substituted for the aryl ring of the standard 3-aryloxy-2-hydroxypropylamines to bring about structural variation.

A series of 3-indolyl-tert.-butylaminopropanols (formula 3) with antihypertensive properties was described in:

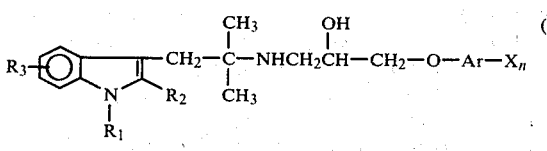

Kreighbaum, et al., U.S. Pat. No. 4,234,595 patented Nov. 18, 1980.

SUMMARY OF THE INVENTION

This invention concerns a series of selective β-adrenergic blocking agents having the general structural Formula (I) or Formula (VI) and the non-toxic pharmaceutically acceptable acid addition salts thereof.

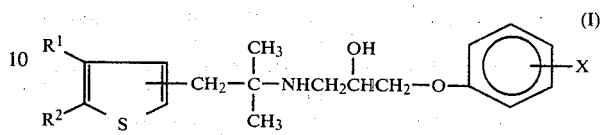

In the foregoing structural Formula (I), $R^1$ and $R^2$ are hydrogen or they are linked together to form a phenylene ring; X refers to substituents on the phenoxy ring and is selected from lower alkyl, lower alkenyl, lower alkynyl, lower alkoxy, lower alkenyloxy, lower alkynyloxy, lower hydroxyalkyl (lower denoting 1 to 4 carbon atoms inclusive); benzyloxy; cyano; acylamino and cyanoalkyl (of 2 to 4 carbon atoms inclusive); cycloalkyl of 3 to 6 carbon atoms; carboxamido; halo; hydrogen; methylthio; nitro; or trifluoromethyl. Preferred compounds have X in the ortho position of the phenoxy ring with the most preferred group being those wherein X is cyano or lower alkyl, particularly methyl. The butylaminophenoxypropanol side chain can be attached to either the 2- or 3- position of the thiophene nucleus.

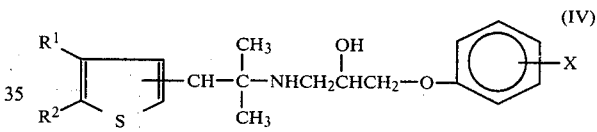

Formula (VI) is the same as Formula (I) except for the phenyloxy ring substituent Y which is selected from amino; hydroxyl; or N-hydroxycarboximido.

DETAILED DESCRIPTION OF THE INVENTION

The invention includes compounds having the foregoing structural Formula (I) and the acid addition salts thereof. The acid addition salts are obtained either by reaction of an organic base of structure (I) with an acid, preferably by contact in solution, or by any of the standard methods detailed in the literature and available to any practitioner skilled in the art.

The compounds of the present invention contain an asymmetric carbon atom in the propanolamine side chain and therefore exist as optically active isomers as well as racemic modifications thereof. The present invention embraces all of these stereoisomeric forms. Resolutions of racemic modifications to provide enantiomers can be carried out using well known methods and standard optically active reagents conventionally employed for this purpose.

Biological testing of the subject compounds of Formula I in animals demonstrates that they possess potent adrenergic β-receptor blocking properties along with intrinsic sympathomimetic activity. These compounds also show β-blocking cardioselectively by virtue of a greater inhibitory effect on increased heart rate than on decreased blood pressure during testing using β-adrenergic stimulation as a challenge in experimental animals. Conventional screening tests were employed for determination of the cardiovascular effect profile of these compounds. Such tests are:

1. Oral administration to rats followed by challenge of the animals with isoproterenol administered intravenously. Isoproterenol is a well known adrenergic β-receptor stimulant which causes an increase in heart rate and a decrease in blood pressure. These effects are antagonized by adrenergic β-receptor blocking agents, and relative potency values are obtained by regression analysis of log dose-response data for the compounds.

2. Intravenous (I.V.) administration to anesthetized dogs with a bilaterally sectioned vagus followed by I.V. isoproterenol challenge. This method is better adapted than the prior test for evaluating β-adrenergic blocking agents which in themselves possess intrinsic sympathomimetic activity. The results of screening selected compounds using this method demonstrated dose-dependent inhibition of the blood pressure and heart rate responses elicited by the isoproterenol challenge. Referring to pre- and post-drug basal rates, these compounds were demonstrated to increase heart rate and decrease blood pressure in their own right.

These cardiovascular effects, as described above for compounds of the instant invention, are associated with a desirable profile for cardiovascular agents useful as hypotensive agents. Therapeutic processes of this invention comprise systemic administration, by both oral and parenteral routes, of an effective, non-toxic amount of a compound of Formula I or a pharmaceutically acceptable acid addition salt thereof to a mammal having a disease state resulting from excessive stimulation of the adrenergic β-receptors, or to a mammal having hypertension. An effective amount is construed to mean a dose which exerts an adrenergic β-receptor blocking action, or antihyperensive action in the effected mammal without undue toxic side effects. Dosage will vary, according to the subject and route of administration selected, with an expected range of about 0.1 mcg to 100 mg/kg body weight of a compound of Formula I or a pharmaceutically acceptable acid addition salt thereof generally providing the desired therapeutic effect.

The compounds of Formula I are prepared by application of known processes (e.g. U.S. Pat. No. 4,234,595—quite illustrative and pertinent procedures found therein and hereby incorporated by reference into this application) to the appropriate starting materials. Specifically, the present invention utilizes a process for preparation of the compounds of Formula I according to the following reaction scheme.

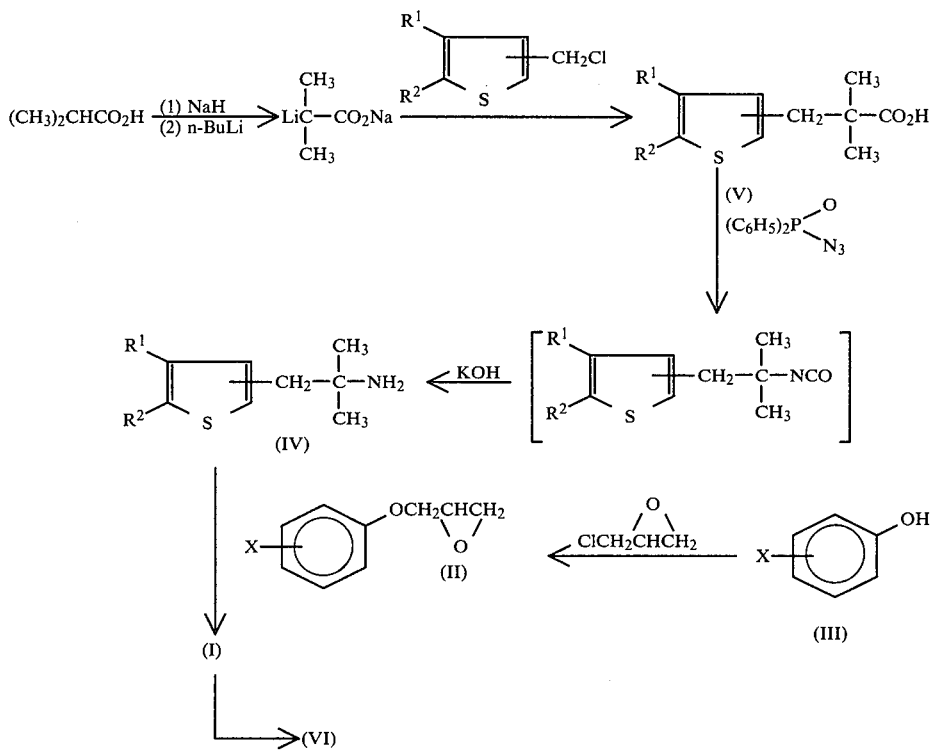

In the foregoing scheme, $R^1$, $R^2$ and X are as defined in Formula I. A further reaction of Formula I compounds in which X is converted to Y produces compounds of Formula VI. The preferred method for making compounds of Formula I involves heating the selected thienyl-tert.-butylamine (IV) with the appropriately substituted epoxypropyl ether (II) in refluxing ethanol under nitrogen for about 12 to 24 hours. This reaction takes place facilely in ordinary laboratory or plant equipment under convenient operating conditions. Preparation of compounds of Formula I according to the process of the invention generally comprises heating II and IV neat or in the presence of a wide variety of reaction inert organic solvents. Suitable solvents include but are not limited to benzene, toluene, tetrahydrofuran, dibutyl ether, butanol, hexanol, methanol, dimethoxyethane, ethylene glycol, etc. Suitable reaction temperatures are from about 60°–200° C. No catalyst or condensation agent is required.

The intermediate epoxypropyl ethers (II) are conveniently prepared by reacting an appropriately substituted phenol (III) with epichlorohydrin in the presence of a catalytic quantity of an amine followed by treating with aqueous alkali metal hydroxide, or conducting the reaction in the first instance in an aqueous alkali metal hydroxide reaction medium whence the amine catalyst is not required.

Heating of epichlorohydrin in substantial molecular excess amount with a phenol containing a drop or two of piperidine as catalyst on a steam bath overnight results in the condensation shown to give (II). Some of the corresponding halohydrin intermediate is also produced and is converted without isolation to (II) by treatment of the mixture with aqueous alkali metal hydroxide. Alternatively, the phenol and epichlorohydrin can be caused to react in the presence of a sufficient amount of a dilute aqueous alkali metal hydroxide to neutralize the acidic phenolic group at room temperature with formation of the desired intermediate (II).

The process leading to preparation of the thienyl-tert.-butylamines (IV) involves treating isobutyric acid with sodium hydride followed by N-butyllithium and then treating the resultant organometallic salt with an appropriately substituted chloromethylthiophene or benzothiophene. Chloromethylthiophene compounds are available commercially or described in the chemical literature with methods of preparation; e.g. see: F. F. Blicke and J. H. Burckhalter, *Journal of the American Chemical Society,* 64, 477 (1942); W. J. King and F. F. Nord, *Journal of Organic Chemistry,* 13, 635 (1948). The resulting thienopropanoic acid (V) is treated first with diphenylphosphorylazide followed by treatment with potassium hydroxide solution to give (IV).

The compounds of the present invention can be formulated according to conventional pharmaceutical practice to provide pharmaceutical compositions of unit dosage form comprising, for example, tablets, capsules, powders, granules, emulsions, suspensions, and the like. The solid preparations contains the active ingredient in admixture with non-toxic pharmaceutical excipients such as inert diluents, for example, calcium carbonate, sodium carbonate, lactose, calcium phosphate or sodium phosphate; granulating and disintegrating agents, for example, maize, starch, or alginic acid; binding agents, for example, starch, gelatin or acacia; and lubricating agents, for example, magnesium stearate, stearic acid or talc. The tablets may be uncoated or they may be coated by known techniques so as to delay disintegration and absorption in the gastrointestinal tract and thereby provide a sustained action over a longer period.

Liquid preparations suitable for parental administration include solutions, suspensions, or emulsions of the compounds of Formula I. The aqueous suspensions of the pharmaceutical dosage forms of the compounds of Formula I contain the active ingredient in admixture with one or more non-toxic pharmaceutical excipients known to be suitable in the manufacture of aqueous suspensions. Suitable excipients are, for example, suspending agents such as sodium carboxyethyl cellulose, methyl cellulose, hydroxypropylmethyl cellulose, sodium alginate, polyvinylpyrrolidone, gum tragacanth, and gum acacia. Suitable dispersing or wetting agents are naturally occurring phosphatides, for example, lecithin, polyoxyethylene stearate.

Non-aqueous suspensions may be formulated by suspending the active ingredient in a vegetable oil, for example, arachis oil, olive oil, sesame oil, or coconut oil, or in a mineral oil, for example, liquid paraffin. The suspensions may contain a thickening agent such as bees wax, hard paraffin, or cetyl alcohol. Sweetening and flavoring agents generally used in pharmaceutical compositions may also be included such as saccharin, sodium cyclamate, sugar and caramel to provide a palatable oral preparation. The compositions may also contain other absorbing agents, stabilizing agents, weighing agents, and buffers.

DESCRIPTION OF SPECIFIC EMBODIMENTS

The compounds which constitute this invention, their methods of preparation and their biologic actions will appear more fully from a consideration of the following examples and appended claims which are given for the purpose of illustration only and are not to be construed as limiting the invention in sphere of scope. In examples which follow, used to illustrate the foregoing processes, temperatures are expressed in degrees centigrade (°). Melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m), or doublet (d). Abbrebiations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group indentification value. The IR determinations were employed using potassium bromide (KBr) as diluent. The elemental analyses are reported as percent by weight.

EXAMPLE 1

2-(2,3Epoxypropoxy)benzonitrile (IIa; X=2-CN)

A solution of 2-cyanophenol (25.0 g., 0.21 mole), epichlorohydrin (117 g., 1.26 mole), and piperidine (10 drops) was stirred and heated at 115°–120° in an oil bath for 2 hrs. The reaction mixture was then concentrated to remove unreacted epichlorohydrin. The residue was diluted with toluene and taken to dryness to remove the last traces of volatile material. The residual oil was dissolved in 260 ml. of tetrahydrofuran, and the solution stirred at 40°–50° for 1 hr. with 260 ml. of 1 normal NaOH. The organic layer was separated and concentrated to an oil which was combined with the aqueous phase. The mixture was extracted with methylene chloride and the extract dried (MgSO$_4$) and concentrated to give 36.6 g. (100%) of oil which slowly crystallized to a waxy solid. This product (IIa) was used without further purification in reactions with compounds of Formula (IV) to give (I). Other epoxypropyl ethers are prepared by using this same procedure with only minor variation.

EXAMPLE 2

2,3-Epoxy-1-(2-methylphenoxy)propane (IIb; X=2-CH$_3$)

A solution of ortho-cresol (64.8 g., 0.6 mole), epichlorohydrin (330 g., 3.6 mole), and piperidine (5 drops) was allowed to react and the product was isolated using the same methods outlined hereinabove in Example 1. Concentration of the methylene chloride extract gave 95 g. of crude epoxide (IIb) which was used without further purification.

EXAMPLE 3

2,2-Dimethyl-3-(2-thienyl)propanoic Acid (Va; $R^1$, $R^2 = H$)

A mixture of 57% oil emulsion of sodium hydride (3.14 g., 0.074 mole), THF (68 ml.) and diisopropylamine (6.87 g., 0.068 mole) was placed under $N_2$. Isobutyric acid (5.98 g., 0.068 mole) was added dropwise. The mixture was heated at reflux for 15 min. to complete formation of the salt. After cooling at 0°, a solution of 1.6 molar n-butyllithium in hexane (42 ml., 0.068 mole) was added in small portions while holding the temperature below 10°. The resulting turbid solution was kept at 0° for 15 min. and then warmed to 30°–35° for 30 min. After again cooling to 0°, 2-chloromethylthiophene (9 g., 0.068 mole) was added dropwise over 15–20 min. while holding temperature between 0° and 5°. The mixture was kept at 0° for 30 min., in the range of 30°–35° for 1 hr. and was then cooled to 15°. Water (90 ml.) was added dropwise and the aqueous layer was separated. The organic phase was washed with a mixture of water (50 ml.) and $Et_2O$ (75 ml.). The aqueous extracts were combined, washed with $Et_2O$ and then acidified with conc. HCl. The oily product was extracted with $Et_2O$ and the combined $ET_2O$ extracts were dried over $MgSO_4$. Evaporation of the $Et_2O$ in vacuo gave 11.4 g. (91%) of product of sufficient purity to be used for conversion into (IVa). The NMR spectrum is consistent with the assigned structure.

EXAMPLE 4

2,2-Dimethyl-3-(3-benzo[b]thienyl)propanoic Acid (Vb; $R^1$, $R^2 = C_4H_4$)

This compound was obtained in 82% crude yield from 3-(chloromethyl )benzo[b]thiophene using the preocedure of Example 3. The yellow viscous oil afforded an NMR spectrum consistent with the assigned structure and was sufficiently pure for subsequent use. TLC on silica plates gave $R_f = 0.7$ (EtOAc).

EXAMPLE 5

α, α-Dimethyl-β-(thienyl)ethanamine (IVa; $R^1$, $R^2 = H$)

A solution of 2,2-dimethyl-3-(2-thienyl)propanoic acid (Va; 11.2 g., 0.06 mole), diphenylphosphorylazide (16.7 g., 0.06 mole) (Aldrich Chemical Company), and triethylamine (6.14 g., 0.06 mole) in tert.-butanol (100 ml.) was heated at reflux for 5 hr. The solution was poured into water (300 ml.) and the crude material extracted with $Et_2O$. The combined extracts were washed with brine, dried over $MgSO_4$ and finally evaporated to get 11.9 g. of crude intermediate. This oil was added to a mixture of ethylene glycol (50 ml.), $H_2O$ (20 drops) and KOH (10 g.). The mixture was heated at reflux for 5 hr., cooled to 25°, diluted with $H_2O$ (300 ml.) and acidified to pH 1 with conc. HCl. A wash with $Et_2O$ removed the acid insoluble material which was discarded. The aqueous solution was made basic with 50% NaOH and the product was extracted with $Et_2O$. The ether extracts were washed with brine, dried over a $MgSO_4$ and evaporated to give 6.9 g. (74%) of product. the NMR spectrum is consistent with the assigned structure.

EXAMPLE 6

α, α-Dimethyl-β-(3-benzo[b]thienyl)ethanamine (IVb; $R^1$, $R^2 = C_4H_4$)

A 71% yield of this compound obtained from (Vb) in a procedure analogous to that of Example 5. The crude oil afforded an NMR spectrum consistent with the assigned structure and was sufficiently pure for use. TLC on silica plates gave $R_f = 0.6$ ($CHCl_3$, $NH_3$).

EXAMPLE 7

1-[3-[[1,1-Dimethyl-2-(2-thienyl) ethyl]amino]-2-hydroxypropoxy]benzonitrile (Ia;-X=2-CN, $R^1$, $R^2 = H$)

A solution consisting of 2-(2,3-epoxypropoxy)benzonitrile (IIa; 3.5 g., 0.02 mole) and α,α-dimethyl-β-(2-thienyl)ethanamine (IVa; 3.1 g., 0.02 mole) in 100 ml. absolute EtOH was heated at reflux under a nitrogen atmosphere for 20 hr. The reaction solution was concentrated to dryness and the residue crystallized on standing. The crystalline residue was recrystallized from ethyl acetate to give 3.8 g. of material, m.p. 90°–96°. This material was decolorized using powdered activated charcoal during a second recrystallization from ethyl acetate. A white crystalline solid was isolated which weighed 2.3 g., m.p. 90°–92°.

Anal. Calcd. for $C_{18}H_{22}N_2O_2S$: C, 65.43; H, 6.72; N, 8.48. Found: C, 65.20; H, 6.81; N, 8.46.

NMR (DMSO-$d_6$): 1.02 (6,s); 1.50 (1,bs); 2.80 (4,m); 3.92 (1,m); 4.16 (2,d); 5.02 (1,bs); 6.90 (2,m); 7.18 (3,m); 7.65 (2,m).

IR (KBr): 690, 760, 1025, 1260, 1285, 1450, 1490, 1600, 2225, and 2930 $cm^{-1}$.

EXAMPLE 8

1-[[1,1-Dimethyl-2-(2-thienyl)ethyl]amino]-3-(2-methylphenoxy)-2-propanol Hydrochloride (Ib; X=2-$CH_3$, $R^1$, $R^2 = H$)

Using the conditions outlined in Example 7, 2,3-epoxy-1-(2-methylphenoxy)propane (8.1 g., 0.05 mole) and α,α-dimethyl-β-(2-thienyl)ethanamine (IVa; 6.9 g., 0.045 mole) were reacted. Recrystallization from acetonitrile gave 10.4 g. of white solid, m.p. 120°–122°.

Anal. Calcd. for $C_{18}H_{25}NO_2S \cdot HCl$: C, 60.74; H, 7.36; N, 3.94. Found: C, 60.81; H, 7.19; N, 3.86.

NMR (DMSO-$d_6$): 1.35 (6,s); 2.21 (3,s); 3.28 (4,m); 4.05 (2,d); 4.36 (1,m); 5.60 (1,bs); 7.01 (6,m); 7.45 ( ,m); 9.00 (1,bs); 9.60 (1,bs).

IR (KBr): 700, 750, 1125, 1250, 1465, 1500, 1590, 1605, 2800, and 2980 $cm^{-1}$.

EXAMPLE 9

2-[3-[[2-(Benzo[b]thiophen-3yl)-1,1-dimethylethyl]amino]-2-hydroxypropoxy]benzonitrile Hydrochloride (Ic; X=2-CN, $R^1$, $R^2 = C_2H_4$)

The procedure for this example is essentially that given in Example 7. A solution consisting of 2-(2,3-epoxypropoxy)benzonitrile (IIa; 1.8 g., 0.01 mole) and α,α-dimethyl-β-(3-benzo[b]thienyl)ethanamine (IVb; 1.6 g., 0.01 mole) in 50 ml. absolute EtOH was heated at reflux under a nitrogen atmosphere for 20 hr. The reaction solution was concentrated to dryness and the residue dissolved in 75 ml. of EtOAc. Upon cooling, a solid crystallized and was isolated by filtration. The solid was washed with cold EtOAc and air dried to give 2.3 g. material, m.p. 131°–132°, which was converted to the hydrochloride salt by dissolving this material in absolute EtOH and acidifying with ethanolic HCl. Reduction of volume and cooling brought about precipitation and 1.6 g. of an off-white solid, m.p. 164°–165°, was isolated by filtration.

Anal. Calcd. for $C_{22}H_{24}N_2O_2S\cdot HCl$: C, 63.38; H, 6.05; N, 6.72. Found: C, 63.44; H, 6.08; N, 6.65.

NMR (DMSO-$d_6$): 1.31 (6,s); 3.40 (4,m); 4.35 (3,m); 6.08 (1,bs); 7.30 (4,m); 7.71 (3,m); 8.07 (2,m); 9.11 (1,bs); 9.65 (1,bs).

IR (KBr): 750, 1110, 1260, 1290, 1450, 1490, 1600, 2225, 2800, and 2980 cm$^{-1}$.

EXAMPLE 10

1-[[2-(Benzo[b]thiophen-3-yl)-1,1-dimethylethyl]-amino]-3-(2-methylphenoxy)-2-propanol Hydrochloride Id; X=2-CH$_3$, R$^1$, R$^2$=C$_4$H$_4$)

Using the conditions outlined in Example 9, 2,3-epoxy-1-(2-methylphenoxy)propane (4.0 g., 0.02 mole) was reacted with α,α-dimethyl-β-3-benzo[b]thienyl)ethanamine (IVb; 4.8 g., 0.02 mole). Recrystallization twice from absolute EtOH gave 6.1 g. of white solid, m.p. 179°–181°.

Anal. Calcd. for $C_{22}H_{27}NO_2S\cdot HCl$: C, 65.09; H, 6.95; N, 3.45. Found: C, 65.11; H, 7.17; N, 3.33.

NMR (DMSO-$d_6$): 1.33 (6,s); 2.23 (3,s); 3.40 (4,m); 4.10 (2,d); 4.41 (1,m); 5.10 (1,bs); 7.07 (4,m); 7.42 (2,m); 7.62 (1,s); 8.06 (2,m); 9.20 (2,bs).

IR (KBr): 750, 1125, 1250, 1460, 1500, 1590, 1605, 2800, and 2980 cm$^{-1}$.

EXAMPLES 11–26

The following compounds of Table A are prepared according to the procedure for Examples 7–10 by reacting (II), the epichlorohydrin derivative of the starting phenol with (IV), a selected thienyl-tert.-butylamine.

TABLE A $$\underset{\underset{S}{\overset{R^1}{\underset{R^2}{\Large\diagup\!\!\!\diagdown}}}}{} -CH-\underset{\underset{CH_3}{|}}{\overset{\overset{CH_3}{|}}{C}}-NHCH_2\underset{\underset{}{}}{\overset{\overset{OH}{|}}{CH}}-CH_2-O-\underset{}{\diagup\!\!\!\diagdown}-X \quad (I)$$

| Example | II<br>X Component | IV<br>Heterocyclic Component | I<br>Name |
|---|---|---|---|
| 11 | 4-CN | 2-benzothienyl | 4-[3-[[2-(benzo[b]thiophen-2-yl)-1,1-dimethylethyl]amino]-2-hydroxypropoxy]benzonitrile |
| 12 | 2-CH$_2$CH=CH$_2$ | 3-thienyl | 1-[[1,1-dimethyl-2-(3-thienyl)ethyl]amino]-3-(1-propen-2-yl phenoxy)-2-propanol |
| 13 | 3-Me | 2-benzothienyl | 1-[[2-(benzo[b]thiophen-2-yl)-1,1-dimethylethyl]amino]-3-(3-methylphenoxy)-2-propanol |
| 14 | 4-NHCCH$_3$ (with C=O) | 2-thienyl | 3-(4-acetamidophenoxy)-1-[[1,1-dimethyl-2-(2-thienyl)ethyl]amino]-2-propanol |
| 15 | 2-Br | 3-thienyl | 3-(2-bromophenoxy)-1-[[1,1-dimethyl-2-(3-thienyl)ethyl]amino]-2-propanol |
| 16 | 2-C≡CCH$_3$ | 3-benzothienyl | 1-[[2-(benzo[b]thiophen-3-yl)-1,1-dimethylethyl]amino]-3-(2-propynylphenoxy)-2-propanol |
| 17 | 2-OCH$_3$ | 2-thienyl | 1-[[1,1-dimethyl-2-(2-thienyl)ethyl]amino]-3-(2-methoxyphenoxy)-2-propanol |
| 18 | 2-CH$_2$OH | 2-benzothienyl | 1-[[2-(benzo[b]thiophen-2-yl)-1,1-dimethylethyl]amino]-3-[2-(hydroxymethyl)phenoxy]-2-propanol |
| 19 | 2-OCH$_2$C≡CH | 3-benzothienyl | 1-[[2-(benzo[b]thiophen-3-yl)-1,1-dimethylethyl]amino]-3-[2-(propargyloxy)phenoxy]-2-propanol |
| 20 | 2-OCH$_2$CH=CH$_2$ | 3-thienyl | 3-[2-(allyloxy)phenoxy]-1-[[1,1-dimethyl-2-(3-thienyl)ethyl]amino]-2-propanol |
| 21 | 4-CH$_2$C(=O)—NH$_2$ | 2-thienyl | 3-[4-(carbamoylmethyl)phenoxy]-1-[[1,1-dimethyl-2-(2-thienyl)ethyl]amino]-2-propanol |
| 22 | 2-C$_5$H$_9$ | 2-thienyl | 3-(2-cyclopentylphenoxy)-1-[[1,1-dimethyl-2-(2-thienyl)ethyl]amino]-2-propanol |
| 23 | 2-SCH$_3$ | 3-benzothienyl | 1-[[2-(benzo[b]thiophen-3-yl)-1,1-dimethylethyl]amino]-3-[2-(methylthio)phenoxy]-2-propanol |
| 24 | 2-CF$_3$ | 3-thienyl | 1-[[1,1-dimethyl-2-(3-thienyl)ethyl]amino]-3-[2-(trifluoromethyl)phenoxy]-2-propanol |
| 25 | 2-NO$_2$ | 2-benzothienyl | 1-[[2-(benzo[b]thiophen-2-yl)-1,1-dimethylethyl]amino]-3-(2-nitrophenoxy)-2-propanol |
| 26 | 2—C(=O)—NH$_2$ | 2-thienyl | 2-[3-[[1,1-dimethyl-2-(2-thienyl)ethyl]amino]-2-hydroxypropoxy]benzamide |
| 27 | H | 2-benzothienyl | 1-[[2-(benzo[b]thiophen-2-yl)- |

TABLE A-continued

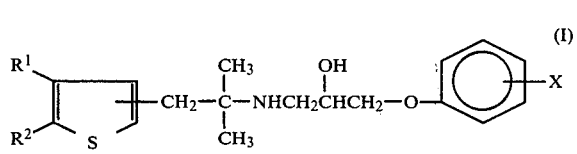

| Example | II<br>X Component | IV<br>Heterocyclic<br>Component | I<br>Name |
|---|---|---|---|
| | | | 1,1-dimethylethyl]amino]-3-phenoxy-2-propanol |
| 28 | 2-CH₂CN | 3-thienyl | 2-[3-[[1,1-dimethyl-2-(3-thienyl)-ethyl]amino]-2-hydroxypropoxy]phenylacetonitrile |
| 29 | 4-OCH₂Ph | 2-thienyl | 3-(4-benzyloxy)-1-[[1,1-dimethyl-2-(2-thienyl)ethyl]amino]-2-propanol |

EXAMPLE 30

1-[[2-(Benzo[b]thiophen-3-yl)-1,1-dimethylethyl-]amino]-3-]2-(N-hydroxy carboximidophenoxy]-2-propanol This compound is conveniently prepared by treating a methanolic solution containing an equivalent of (Ic) as the free base with two equivalents of hydroxylamine base in methanol and then refluxing for 12-24 hrs. Concentration in vacuo to a residue and crystallization from alcohol will yield the desired product.

EXAMPLE 31

3-[2-Aminophenoxy)-1-[[2-benzo[b]thiophen-2-yl)-1,1-dimethylethyl]amino]-2-propanol This compound is conveniently prepared by catalytic hydrogenation of the product of Example 25 using standard hydrogenating conditions and catalysts familiar to anyone skilled in the chemical art.

EXAMPLE 32

1-[[1,1-Dimethyl-2-(2-thienyl)ethyl]amino]-3-(4-hydroxyphenoxy)-2-propanol

This compound is conveniently prepared by catalytic hydrogenolysis of the product of Example 29 using standard hydrogenolysis conditions with a Pd on carbon catalyst.

What is claimed is:

1. A compound selected from the group consisting of a compound having Formula (I)

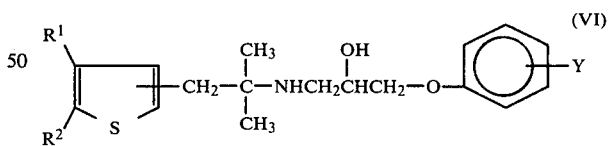

wherein

X is lower alkyl, lower alkenyl, lower alkynyl, lower alkoxy, lower alkenyloxy, lower alkynyloxy, lower hydroxyalkyl (lower denoting 1 to 4 carbon atoms inclusive); benzyloxy; cyano; acylamino and cyanoalkyl (of 2 to 4 carbon atoms inclusive); cycloalkyl of 3 to 6 carbon atoms; carboxamido; halo; hydrogen; methylthio; nitro; or trifluoromethyl;

R¹ and R² are hydrogen or they are linked together to form a phenylene ring; and the butylaminophenoxypropanol side chain is attached to either the 2- or 3- position of the thiophene nucleus.

2. The compounds of claim 1 wherein X is attached to the ortho position of the phenoxy ring.

3. The compound of claim 1, 2-[3-[[1,1-dimethyl-2-(2-thienyl)ethyl]amino]-2-hydroxypropoxy]benzonitrile (Ia) or a pharmaceutically acceptable acid addition salt thereof.

4. The compound of claim 1, 1-[[1,1-dimethyl-2-(2-thienyl)ethyl]amino]-3-(2-methylphenoxy)-2-propanol (Ib) or a pharmaceutically acceptable acid addition salt thereof.

5. The compound of claim 1, 2-[3-[[2-(benzo[b]thiophen-3-yl)-1,1-dimethylethyl]amino]-2-hydroxyproxy]-benzonitrile (Ic) or a pharmaceutically acceptable acid addition salt thereof.

6. The compound of claim 1, 1, 1-[[2-(benzo[b]thiophen-3-yl)-1,1-diemthylethyl]amino]-3-(2-methyl-phenoxy)-2-propanol (Id) or a pharmaceutically acceptable acid addition salt thereof.

7. A compound selected from the group consisting of a compound having Formula (VI)

wherein

Y is amino; hydroxyl; or N-hydroxycarboximide;

R¹ and R² are hydrogen or they are linked together to form a phenylene ring; and the butylaminophenoxypropanol side chain is attached to either the 2- or 3- position of the thiophene nucleus.

* * * * *